United States Patent [19]
Edmondson

[11] Patent Number: 6,129,895
[45] Date of Patent: Oct. 10, 2000

[54] FUEL ADDITIVE ANALYZER SYSTEM AND PROCESS

[75] Inventor: Farrell R. Edmondson, Sarasota, Fla.

[73] Assignee: Emcee Electronics, Inc., Venice, Fla.

[21] Appl. No.: 08/105,643

[22] Filed: Aug. 12, 1993

[51] Int. Cl.[7] .......................... B32B 27/04; B32B 27/12; B32B 5/02
[52] U.S. Cl. .......................... 422/78; 204/406; 204/407; 422/82.02; 422/82.12; 436/137
[58] Field of Search ................... 422/78, 82.01, 422/82.02, 82.12; 436/132, 136, 128, 137, 150, 151; 204/400, 406, 407, 408, 153.16, 153.2; 324/663, 674, 675, 681, 682

[56] References Cited

U.S. PATENT DOCUMENTS

| | | | |
|---|---|---|---|
| 3,753,092 | 8/1973 | Ludlow et al. | 324/663 |
| 4,370,611 | 1/1983 | Gregory et al. | 324/663 |
| 4,555,661 | 11/1985 | Benson et al. | 324/682 X |
| 4,675,596 | 6/1987 | Smith | 324/674 X |
| 4,939,467 | 7/1990 | Noglami et al. | 324/663 |
| 5,005,402 | 4/1991 | Pischinger et al. | 324/663 X |
| 5,091,704 | 2/1992 | Kopera | 331/65 |
| 5,103,181 | 4/1992 | Gaisford et al. | 324/637 |
| 5,124,654 | 6/1992 | Scheid | 324/663 X |
| 5,134,380 | 7/1992 | Jonas | 324/674 |
| 5,134,381 | 7/1992 | Schmitz et al. | 324/685 |
| 5,182,523 | 1/1993 | Ertel et al. | 324/663 |
| 5,196,801 | 3/1993 | Nogami et al. | 324/663 |
| 5,231,358 | 7/1993 | Kapsokavathis | 324/663 X |
| 5,247,287 | 9/1993 | Jonker et al. | 345/134 |
| 5,262,730 | 11/1993 | Smith et al. | 324/650 |

*Primary Examiner*—Robert J. Warden, Sr.
*Attorney, Agent, or Firm*—Donald R. Fraser

[57] ABSTRACT

An oxygenate additive analyzer is provided which detects and determines the presence of oxygen enhancing additives in gasoline or other fuels. The oxygenate additive analyzer includes a portable electronic controller with a fuel cell connected to the controller by a ribbon cable. In operation, a sample of the fuel to be tested is placed in the fuel cell and electrical control signals are transmitted between the controller and the fuel cell. The analyzer measures the direct current conductivity, resonant frequency, and temperature, and such data is analyzed on the unique software system in the microprocessor of the controller. Upon the completion of the fuel analysis, the controller displays the percentage, if any, of added oxygen by weight, lists probable oxygenates as a percentage of volume, and shows the temperature of the fuel sample. The analyzer is a portable unit with a battery power supply. The batteries are rechargeable from both a 120 volt Ac power supply or a 12 volt DC automobile battery-power system. The analyzer includes a computer interface and printer connector to facilitate communication of the information to an external computer and/or printer for logging and storage of information.

7 Claims, 4 Drawing Sheets

FUEL ADDITIVE ANALYZER SYSTEM AND PROCESS

BACKGROUND OF THE INVENTION

1. Field of the Invention. The present invention relates to a fuel additive analyzer system and process, and more particularly to an improved apparatus for, and method of, determining the presence of oxygen enhancing additives in a fuel supply and the oxygen content of such fuel supply by weight.

2. Summary of Related Art. The enactment of the Federal Clean Air Act Amendments of 1990 requires the each state to sell oxygenated gasoline in areas where the air quality does not meet the federally mandated National Ambient Air Quality Standards (the "Standards"). This requires certain metropolitan areas with high levels of carbon monoxide and other air pollutants to sell, during the portion of a year in which the area is prone to high concentration of air pollutants, fuels containing such levels of oxygen as necessary to provide for attainment of the Standards. The addition of oxygen to the fuel supply results in a cleaner burning fuel with less air contamination.

The Standards are effective in 1993 and the state and federal governments are working to identify the metropolitan areas that do not meet the Standards. As additional metropolitan areas fail to meet the Standards, the requirements for supplying oxygenated fuel will increase throughout the United States.

A number of additives have been approved for supplying the additional oxygen to the fuel supply. However, the primary additives in use are (1) Ethyl Alcohol and (2) Methyl Tertiary Butyl Ether ("MTBE"). The amount of oxygen to be added to the gasoline varies depending on the level of contaminants in the fuel and other steps being taken to improve the quality of the air. However, in the metropolitan areas not in compliance with the Standards, the statutory and regulatory provisions require the fuel supply must have the specified oxygen levels in order to permit the sale of the fuel.

At this time, there is a need for a convenient, accurate, and reliable means for testing and documenting the oxygen additives in gasoline and other fuels. A portable analyzer would be used not only by government inspectors for compliance purposes, but also by service stations, oil companies, and independent consultants to test and independently document compliance with the Standards.

Oxygen content in oxygenated gasoline has historically been measured by gas chromatography or infra-red spectrophotometry. Both of these methods are quite complex and require calibration based on a blended reference sample using the additive type which is in the fuel being tested. In addition, these methods are also more conducive for laboratory and production oriented testing, and not for portable use in testing oxygen levels at service stations and other field locations.

The present invention utilizes dielectric properties of the additives, and resonant frequency and DC conductivity measurements to determine the composition of the fuel being tested. The fuel dielectric constant is a function of the oxygen level in the fuel and the additives used to achieve such oxygen level. A microprocessor programmed with a special algorithm may be used to identify the additives in the fuel and the percentage weight of such additives.

A number of monitoring systems have been developed for use in automobiles, and in other applications, for monitoring air-fuel ratios and fuel compositions. U.S. Pat. No. 4,389,881 to Butler et al discloses a method for determining an air to fuel ratio for an internal combustion engine by measuring the electromotive force of an oxygen sensor, the total pressure of a sample gas stream, and the known oxygen addition rate.

U.S. Pat. No. 4,578,172 shows a detector for use in measuring the concentration of oxygen in exhaust gas from a burning device, such as an internal combustion engine or gas burner. An oxygen sensor is used to detect the change in electromotive force that is produced by the difference between the partial oxygen pressure of the exhaust gas and that of atmospheric air.

The air fuel ratio detector disclosed in U.S. Pat. No. 4,629,535 to Oyama et al. includes an oxygen ion conductive solid electrolyte, first and second electrodes on each side of the electrolyte, a diffusion resistor exposed to the measured gas, and means for supplying a current between the first and second electrode. The withdrawal current value is used to determine the air-fuel ratio.

U.S. Pat. No. 5,103,184 to Kapsokavathis et al teaches a fuel composition sensor apparatus for signaling an engine control computer in an automobile operating on an unknown, variable concentration of two fuels, such as gasoline and alcohol.

U.S. Pat. No. 5,103,181 to Gaisford et al discloses a system and process for determining the compositional makeup of multicomponent fluids, solids, and mixtures thereof whose components have different electrical impedance properties. The system is suitable for use in a variety of industrial processes where the fluids and solids may be stationary, moving in batches, or flowing continuously. Radio frequency bridge techniques are used to parameterize the complex dielectric properties of the components in an electrically isolated, physically open structure.

SUMMARY OF THE INVENTION

In accordance with the present invention, there is provided an oxygenate additive analyzer which detects and determines the presence of oxygen enhancing additives (referred to as oxygenates) in gasoline or other fuels. The oxygenate additive analyzer of the present invention consists of a portable electronic controller with a fuel cell connected to the controller by a ribbon cable.

In operation, the additive analyzer takes a sample of the fuel to be tested in the fuel cell. Electrical control signals are transmitted between the controller and the fuel cell and resonant frequency and DC conductivity measurements are obtained and analyzed by a microprocessor. Upon the completion of the fuel analysis, the controller displays the percentage, if any, of added oxygen by weight, lists probable oxygenates as a percentage of volume, and shows the temperature of the fuel sample. If the fuel sample cannot be analyzed for any reason, the analyzer provides an indication of such status. The analyzer is a portable unit with a battery power supply. The batteries are rechargeable from both a 120 volt Ac power supply or a 12 volt DC automobile battery-power system. The analyzer is simple to operate and a test is completed in five minutes or less. These features combine to make the analyzer of the present invention ideal for field testing and analysis.

The oxygenate additive analyzer is able to interface with a computer and includes a display screen and printer output to facilitate data logging and analysis. The test data can be stored in a computer memory or hard copies can be printed on the free standing printer to show compliance with the EPA Fuel Additive Regulations of the Clean Air Act.

In the present invention, the fuel cell is used to measure the direct current conductivity, the resonant frequency, and the temperature of a fuel sample in the fuel cell. The data from the fuel cell is amplified and transmitted to the control circuits in the controller. The data is converted to digital signals and is analyzed by a microprocessor having a unique software program developed for the analyzer. The algorithm of the software program calculates the dielectric constant and an oxygen factor for the fuel sample.

After the analysis is complete, the controller displays percentage of added oxygen by weight, oxygenates as a percentage of volume, and sample temperature. The analyzer includes a computer interface and printer port connector to facilitate communication of the information to an external computer and/or printer. The controller is provided with the necessary computer software for data logging and tracking.

An object of the present invention is to provide an oxygenate additive analyzer which is simple to use. The test for compliance with the oxygenate additive regulations will be conducted in the field in most cases. The instruments must be rugged and easy to set up and use.

A further goal of the present invention is to provide a timely test result. Taking fuel samples to a laboratory for testing is not practical in most cases. An immediate response is preferred in order to insure compliance with the oxygenate additive requirements.

An additional object of the present invention is to provide an analyzer that is furnished with a computer program for data logging and analysis. Generating the proper documentation is an important part of the compliance procedures under the Clean Air Act.

A further object of the present invention is to provide a low cost piece of equipment that will provide accurate results for the intended use. By further calibration of the system, an operator will be able to increase the accuracy of the system. The system will also be suitable for use on fuels other than gasoline, which can be programmed into the microprocessor of the controller.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
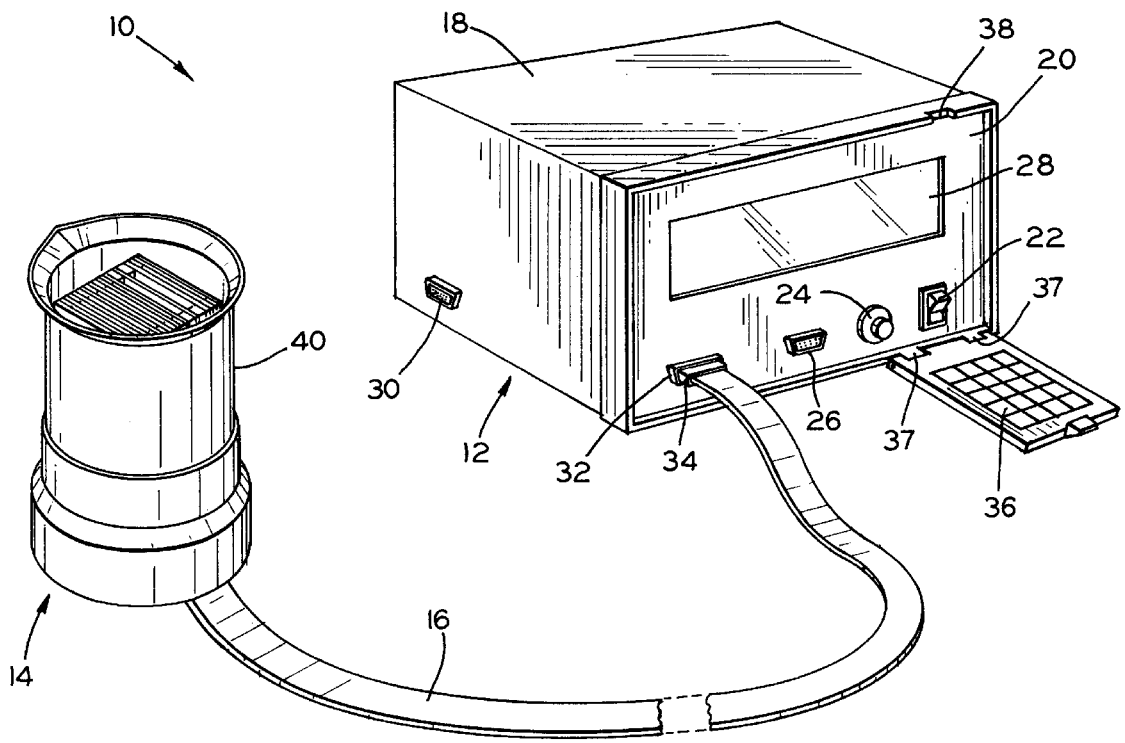
FIG. 1 is perspective view of the fuel cell, controller, and ribbon cable for the fuel additive analyzer of the present invention.

Referring now to the drawings, there is illustrated in FIG. 1 the fuel oxygenate additive analyzer system 10 of the present invention, including the controller 12, the fuel cell 14, and the interconnecting ribbon cable 16.

The controller 12 includes a standard metal enclosure 18 for enclosing the power supply, the control circuits, the microprocessor, and other components. The front panel 20 of the controller 12 includes a power switch 22 for turning power on and off, a start push button 24 to initiate various operational steps during the analysis, and a connector 26 for connecting a computer to the controller 12. The controller 12 is provided with an alpha-numeric, liquid crystal readout 28 for displaying instructions and test results to the operator.

An output port connector 30 is also provided on the controller 12 for connection to an optional printer (not shown), which permits a hard copy of the test results to be printed on the printer. The controller 12 includes three power receptacles (not shown in FIG. 1) for supplying 120 and 240 volts AC, and 12 volts DC to the controller 12.

The front panel 20 of controller 12 also includes a connector 32 for receiving the connector 34 on one end of the ribbon cable 16. The ribbon cable 16 is a standard computer ribbon cable and includes a connector on the opposite end for connection to the fuel cell 14.

The final item mounted on the front panel 20 of the controller 12 is the keyboard 36. The keyboard 36 is a numeric keyboard for calibrating the system 10 and for entering other input parameters into the control circuits and microprocessor of the controller 12. The keyboard 36 is pivotably connected to the controller 12 at pivot points 37 and latches at shoulder 38. The keyboard 36 is pivoted to a closed position when the system 10 is not in use.

Figure 2:
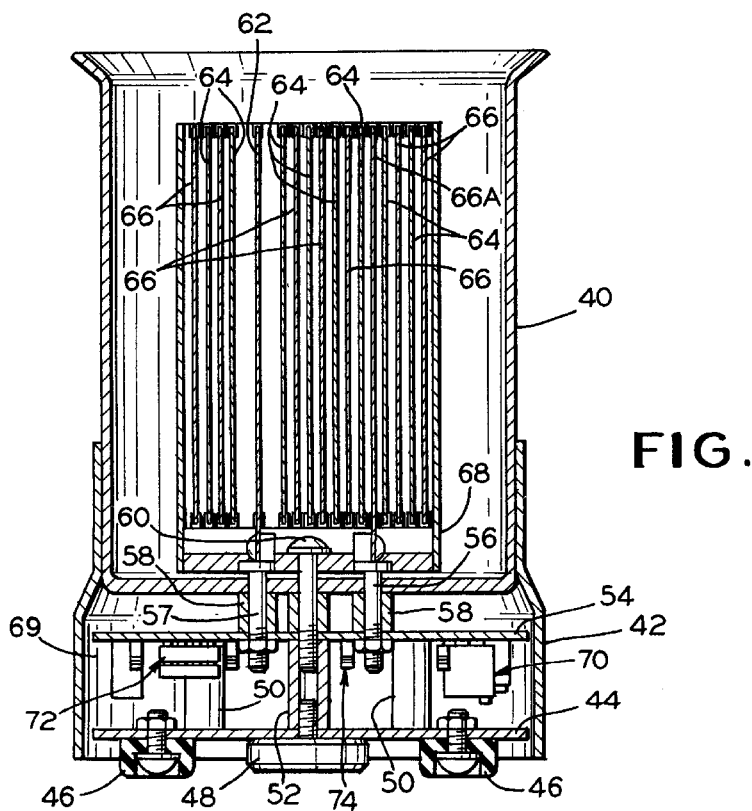
FIG. 2 is a side elevational view, in full cross-section, showing the internal components of the fuel cell.

The fuel cell 14, as shown in FIG. 2, includes a container 40 for receiving and retaining the fuel sample and a cover (not shown) to close the fuel cell at the start of the analytic procedures. A side shield 42 is used to protect the components at the bottom of the fuel cell 14.

The base 44 of the fuel cell 14 is elevated by mounting hubs 46 which are bolted to the base 44. The connector 48 is mounted on the bottom of the base 44 and is connected to the connector on the cable 16 to facilitate electrical communication between the controller 12 and the fuel cell 14.

Extending from the base 44 are side support rods 50 and center support 52, which support the pre-amp circuit board base 54. Terminal bolts 56, 57 and insulators 58 are used to support and secure the container 40 on top of the circuit board 54. The thermocouple terminal probe 60 is secured on the bottom of the fuel cell container 40 as shown in FIG. 2. The thermocouple probe 60 receives a DC control voltage signal from the controller 12 and transmits a temperature related signal back to the controller 12 in the known manner.

The electrode plates 62, 64, 66 are positioned in the container 40 of the fuel cell 14. The plates are maintained in a frame 68 made of teflon or other suitable material. Electrode plate 62 is the DC conductivity plate and is connected to terminal bolt 57. Plate 66A is connected to terminal bolt 56 and is used to provide the oscillating input to the fuel cell 14. The plates 62, 64, 66 and terminal bolts 56, 57 are made from stainless steel or other suitable material for fuel cell operation. The electrode plates 62, 64, 66 are similar except for their electrical interconnection.

The fuel cell utilizes four stainless steel spring pins (not shown) inserted through slots in the lower end of the electrode plates 62, 64, 66 at the bottom of the frame 68 in container 40. The steel pins selectively engage the plates to electrically interconnect the plates as shown in the electrical schematic in FIG. 3, which facilitates the receiving and transmitting of control signals to the controller 12 for processing. In FIG. 1, the spring pins electrically connect a first set of electrode plates 66 in parallel and a second set of electrode plates 64 in parallel. The electrode plates 64 and 66 are arranged generally in alternating sequence in the frame 68 of the container 40. The spring pins are fixed to engage the desired plates for electrical interconnection and to pass through the slots in plates where interconnection is not required.

The electrode plates 64, 66 are used to receive an oscillating input signal from the controller 12 and to transmit a resonant frequency signal, which varies depending on the type of fuel and additives in the fuel, to the controller 12. The DC conductivity electrode plate 62 is an independent plate and is not electrically interconnected to either electrode plates 64 or electrode plates 66. The DC conductivity electrode plate 62 transmits signals to the controller 12, the signal varying with the DC conductivity of the fuel in the container 40 of the fuel cell 14.

The electrical control components of the fuel cell 14 are mounted on circuit board 54 in gap 69 between the circuit board 54 and the base 44. The three fuel cell electrical circuits include the phase locking oscillator circuit 70 for generating the resonant frequency, the conductivity converter circuit 72 for converting the output from the DC conductivity probe 62 to a voltage signal, and a temperature converter circuit 74 for converting the output from the thermocouple 60 to a voltage signal.

Figure 3:
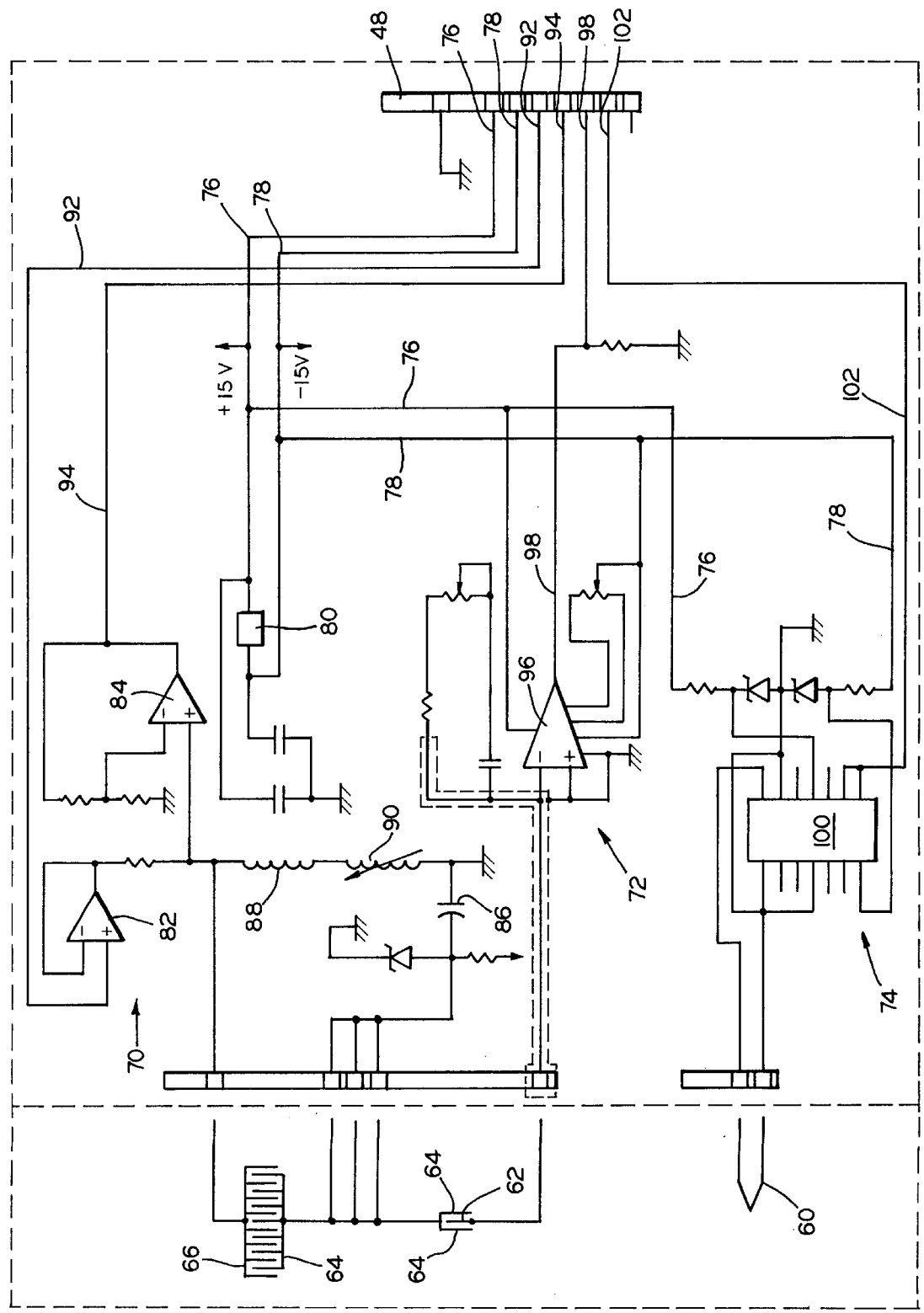
FIG. 3 is a an electrical schematic diagram for the fuel cell circuit.

FIG. 3 shows the electrical schematic for the phase locking oscillator circuit 70, the conductivity converter circuit 72, and the temperature converter circuit 74. The connector 48 is connected to the controller 12 to provide a +15 volts DC on power line 76 and −15 volts DC on power line 78. The DC power supply is furnished to all three circuits.

The phase locking oscillator circuit 70 is provided with a supply voltage circuit 80 for supplying voltage to amplifier 82 and amplifier 84. The circuit 70 includes an LC oscillating circuit with capacitor 86, inductor 88, and variable inductor 90. The input signal for the oscillator circuit 70 is supplied by the controller 12 through lead 92 extending from connector 48. The resonant frequency output signal from the oscillator circuit 70 is transmitted through lead 94 to the controller 12.

The conductivity converter circuit 72 shows amplifier 96 connected to the DC conductivity electrode plate 62. The conductivity range for the circuit is 0–50,000 pico siemens per meter. The converter system 72 generates a voltage signal which is transmitted through lead 98 to the controller 12.

The thermocouple 60 is connected to the temperature converter circuit 74. The integrated circuit chip 100 converters the signal from the thermocouple to an output voltage signal for transmission on lead 102 to the controller 12.

In summary, the fuel cell 14 and connector 48 connect the phase locking oscillator circuit 70, the conductivity converter circuit 72, and the temperature converter circuit 74 to the controller 12. The controller 12 transmits DC power through leads 76,78 and an oscillating input signal through lead 92. The fuel cell 14 receives the operating power and oscillating signal and transmits to the controller 12 a resonant frequency control signal on lead 94, a DC conductivity control signal on lead 98, and a temperature control signal on lead 102.

Figure 4:
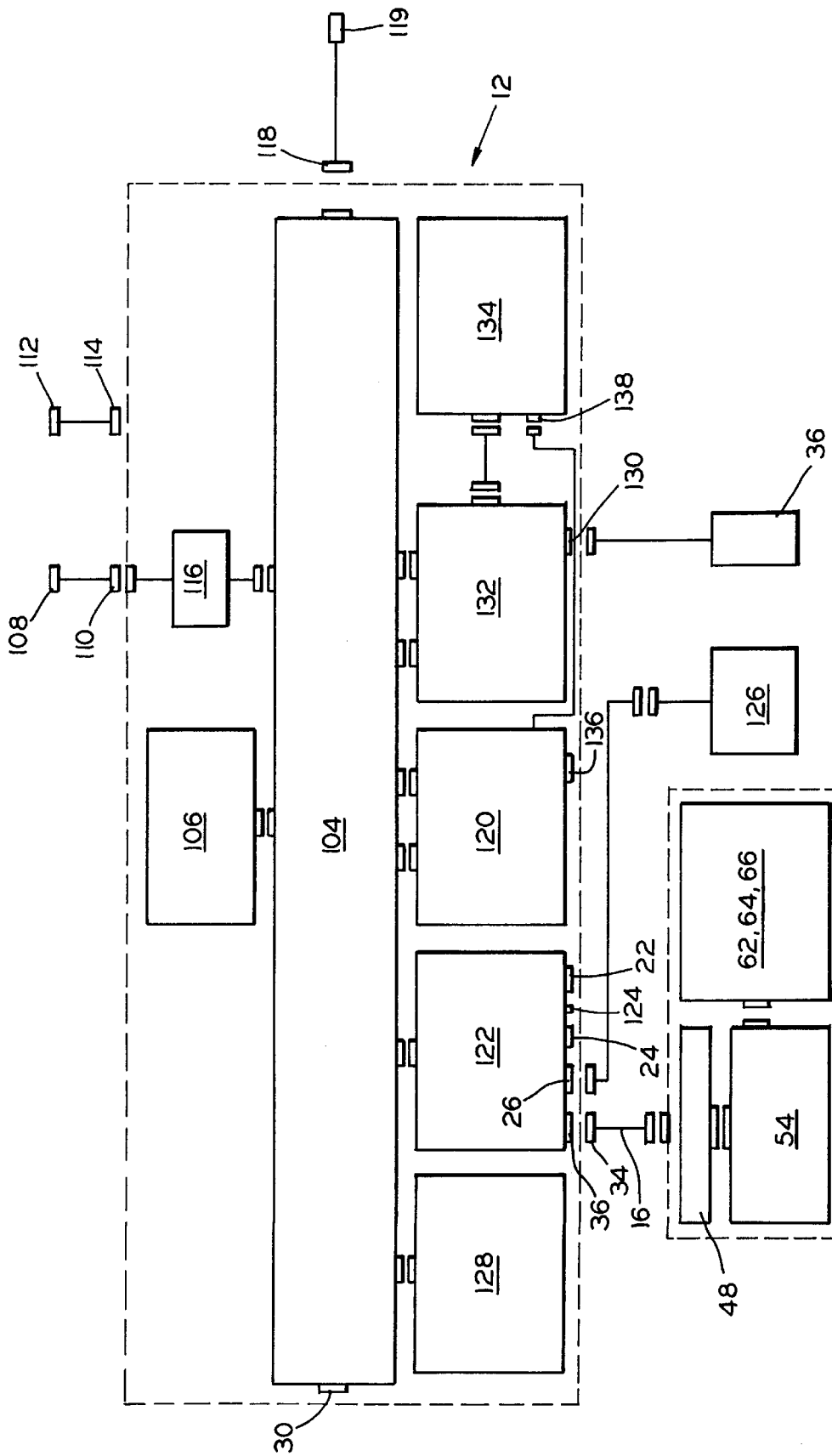
FIG. 4 is a schematic diagram in block form showing the primary components of the fuel cell and controller for the analyzer.

FIG. 4 shows a block diagram of the circuit layout in the controller 12 and fuel cell 14. The fuel cell 14 includes the plates 62, 64, 66 connected through the circuit board 54 to the connector 48 and cable 16 to the controller 12.

In the controller 12, the mother board 104 facilitates the delivery of power to the various circuits and the transmission of data signals between the circuits in the controller.

The controller 12 has a number of power source options to provide the DC voltage for operation. An internal nickel-cadmium battery pack 106 is provided as the primary source of power for portable field operation. The controller 12 will operate for approximately 4 hours between charges. The typical battery pack 106 includes 12 size C batteries. In addition to the battery pack 106, the controller 12 may also be operated from AC power utilizing standard 120 and 240 volt power supplies. The 120 volt supply 108 is received at port 110 on the back of the controller housing 18 and the 240 volt supply 112 is received at port 114. Both power supplies are connected to a transformer 116 which converts the AC power to the desired DC power supply.

A 12 volt DC input jack 118 permits the instrument to be operated from a vehicle cigarette lighter 119. The battery pack 106 is charged when the controller 12 is connected to the external power supplies.

The 12 volt DC power is supplied to the power board 120. The power board 120 generates the +15 volts and −15volts DC power supplied for operation of the fuel cell 14 and other power components in controller 12, and also generates the +5 volts DC voltage used for control purposes.

The printer port 30 is also shown in FIG. 4. The port 30 is a RS-232 serial output port at 1200 Baud. When the test results are displayed on the liquid crystal diode display 28, the results are also transmitted to port 30 for printing a hardcopy report at an optional thermal printer (not shown).

The circuit board in communication with the fuel cell 14 is the phase lock loop (PLL) board 122. The PLL board 122 is provided with terminals for receiving signals from the power switch 22 and the start button 24. An indicating light output connector 124 is provided to power a light emitting diode LED in the power switch 22. The LED is turned on when power switch 22 is on and sufficient power is available to conduct the analysis. A constant light indicates a DC source in use and a flashing light indicates that an Ac power supply is being used to power the controller 12.

The PLL board 122 supplies the 15 volt DC power supply from the power supply board 120 to the various components in the fuel cell 14. An oscillating input signal is generated by components on the PLL board 122. The oscillating signal is transmitted to the fuel cell 14 as noted above and the resonant frequency response signal is received at a counter circuit on the PLL board 122 to count and calculate the resonant frequency. The PLL board 122 also receives conductivity and temperature signals from the fuel cell 14. The signals are amplified and converted to an analog voltage signal.

The console board 128 includes two converter circuits for converting an analog signal to a digital signal. The output signals from the PLL board 122 and console board 128 include a frequency count of the resonant frequency, the digital signal for the conductivity measurement, and the digital signal for the temperature. The data is taken over a period of time and the average data is used as the basis for analysis. The console board 128 includes a data multiplexer and serial converter to average the data and generate the necessary data signals for transmission of information to the microprocessor 132 and to a personal computer 126 through connector port 26.

The microprocessor 132 receives the resonant frequency data, the DC conductivity data, and the temperature data from the fuel cell 14, plus input data from keyboard 36, through the PLL board 122 and the console board 128. Input signals are also received from the keyboard 36 at port 130 for processing calibration information and other performance and correction factors entered from the keyboard 36.

The serial data connector port 26 facilitates the communication of the same data to an external personal computer 126. Software for the personal computer 126 is supplied with the system 10, which permits the personal computer 126 to perform a data analysis simultaneously with the internal microprocessor 132. A computer program has been developed by the applicant to process and analyze the data received at the microprocessor 132 and the personal computer 126. The software for the personal computer 126 allows the inputting of fuel sample codes and comments which can be saved on disk for recording and future analysis. A hardcopy of the results of the analysis may also be printed on a printer (not shown) connected to the personal computer 126.

After the analysis is complete, the microprocessor 132 has determined the percentage of added oxygen by weight, oxygenates as a percentage of volume, and sample temperature. Before discussing the logic sequence of the program as shown in FIG. 5, the remaining components of the controller 12 will be considered.

The output from the microprocessor 132 is transmitted to port 30 for printing a copy of the results and to display board 134 for displaying the results on the liquid crystal display 28. The liquid crystal display 28 may be difficult to read in an outdoor setting and a contrast control adjustment knob 136 is provided on the power board 120. A signal is sent from the power board 120 to the display board 134 and backlight 138 of the display 28 to adjust the intensity of the display 28.

Figure 5:
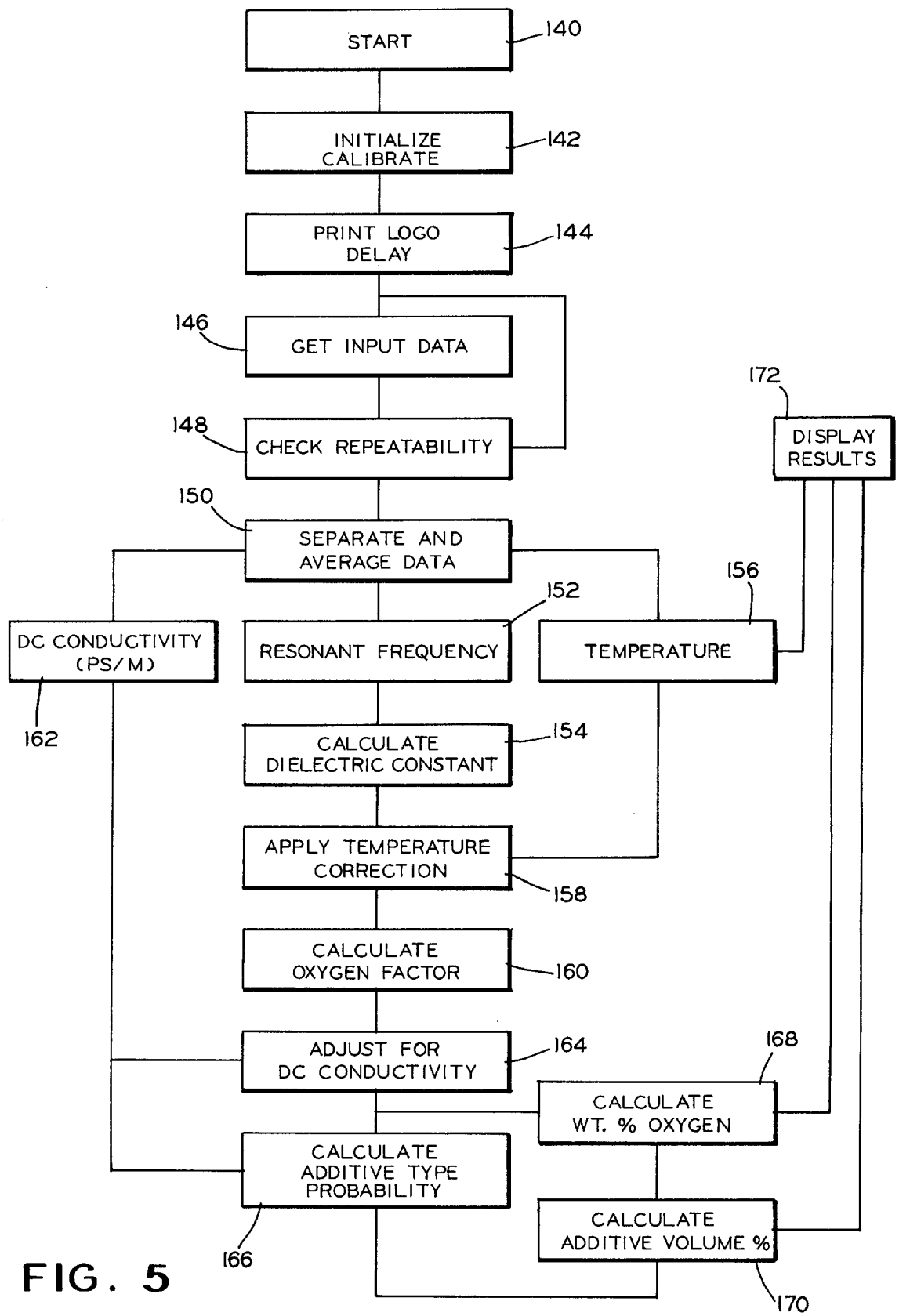
FIG. 5 is a block diagram showing the operational steps of the microprocessor algorithm for the analyzer.

FIG. 5 shows the particular process analysis algorithm which is programmed for use in the microprocessor 132 and the external personal computer 126. In oxygenated gasolines, the fuel dielectric constant is a function of the oxygen level. The two primary additives, ethyl alcohol and MTBE, do not generate the same dielectric constant for a specific oxygen content. The combination of DC conductivity and dielectric constant with corrections for sample temperature provide a unique method for measurement of the oxygen content of a fuel and for distinguishing among the primary additives used to oxygenate fuel.

The first step in the process is called the start phase 140. The power is turned on and a signal is received to start the testing procedures. The next step is to initialize and calibrate the system 142. The analyzer is first tested with an empty fuel cell 14, which is commonly referred to as a clean test. By sending out an oscillating signal and measuring the resonant frequency and the DC conductivity, the microprocessor 132 determines whether there are any contaminants present in the fuel cell 14. The microprocessor 132 sends a signal to the display 28 when contaminants are present to indicate that the fuel cell 14 needs to be cleaned. The clean test sequence with an empty fuel cell 14 does not need to be run before each test, but such a sequence should be run on a regular basis to confirm the non-contaminated status of the fuel cell 14.

In addition to the initial clean test for fuel cell contaminants, there are optional calibration values which can be programmed into the microprocessor 132. Although calibration is not necessary to operate the system 10, such calibration will improve the accuracy of the test results. Each refinery and each batch of crude oil results in gasoline and fuels which are have slightly different chemical and electrical properties. The differences are more pronounced when considering an east coast refinery utilizing crude oil from the Middle East and a west coast refinery using crude oil from Alaska. The keyboard 36 is used to input information to calibrate the system. The microprocessor 132 has fuel and additive variables programmed into the system, and certain variables, such as the specific gravity of the fuel, may be changed to improve the accuracy of the testing.

If a sample of the base stock prior to adding additives is available, the base stock may be placed in the fuel cell and tested to calibrate the system. The keyboard 36 may also be used to set default values, input specific gravity data, and input other information into the microprocessor 132. For example, a fuel other than gasoline may be tested by entering information through the keyboard 36 to the microprocessor 132. In addition, information regarding the actual additives which are supposed to be in the fuel sample may be entered into the system 10.

After the system 10 is initialized and calibrated (step 142), the display 28 provides instructions to the operator to fill the fuel cell 14 and start the testing 144. An oscillating input signal is sent to the fuel cell 14 and the resonant frequency, DC conductivity, and temperature signals from the fuel cell 14 to the PLL board 122 and the console board 128 are measured and stored in the microprocessor 132 (step 146). The test sequence for such a procedure takes approximately 10 seconds. The same test procedures are repeated three times and the results are compared (step 148) to ensure the repeatability and accuracy of the test.

The results of the three tests are averaged and the DC conductivity, resonant frequency, and temperature signals are separated 150 for further analysis and processing. The resonant frequency value 152 is used to calculate the dielectric constant 154 of the fuel being tested. The next step 156 involves converting the temperature signal to an output display signal. Because the dielectric constant is dependent on temperature, it is also necessary to correct the dielectric constant determined in step 154 by applying a temperature correction factor 158.

After the temperature correction factor has been applied, the dielectric factor is used to calculate the oxygen factor 160 in the fuel sample. The DC conductivity signal 162 is used in the microprocessor to adjust the oxygen factor based on the DC conductivity data 164. After such an adjustment, the weight percentage oxygen is calculated for display 168.

In addition to the weight percentage oxygen, the microprocessor 132 also calculates the probable additive type 166 and the additive volume as a percentage of volume 170. If more than one oxygenate additive is present, the output will list the additive present and percentage volume required for that additive to be present.

The temperature, the weight percentage oxygen, and the additive volume are then displayed 172 on the display 28 to complete the basic testing process.

A printer may be connected to the controller 12 to permit a hard copy of the test results to be printed. The printer will list the same test result information as is shown on the liquid crystal display 28.

A personal computer 126 may also be connected to the controller 12 as previously noted. The computer software containing the process analysis algorithm is generally furnished on diskette to provide the user with significant flexibility in using the system 10. A similar analysis takes place in the computer 126 as in the internal microprocessor 132. Information may be stored in the personal computer along with the test results to improve the documentation and future utility of the test information. Information such as the fuel type, location of fuel and testing, and company information may be stored. Each test is assigned a file and the tested results are sorted by the time of the test. The results may also be stored and accessed in the personal computer in other fashions, such as by name of owner or location of the fuel sample.

To operate the analyzer system 10, the power switch 22 is turned on. The LCD display 28 is adjusted to provide the best viewing contrast depending on the lighting conditions and the angle of viewing.

The next step is to run a clean test and calibrate the analyzer 10, as noted above. Once the fuel cell 14 is deemed to be clean, the fuel test can be conducted The fuel cell 14 is filled until the plates 62, 64, 66 are covered by the fuel to be tested. The start button 24 is actuated to commence the testing procedure. The display 28 indicates when the first, second, and third series of tests are being performed. If the test data is not within the repeatability limits programmed into the microprocessor 132, the controller 12 will return to the first test to repeat the series of tests.

After the tests are completed and the microprocessor 132 has analyzed the results, the display 28 of controller 12 displays the percentage, if any, of added oxygen by weight, lists probable oxygenates as a percentage of volume, and shows the temperature of the fuel sample. If the fuel sample cannot be analyzed for any reason, the analyzer provides an indication of such status.

The test results are also available for storage on a personal computer 126 or for printing on an external printer.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A portable fuel oxygenate additive analyzer system for field testing and analyzing oxygen and additive content in samples of fuels comprising:

a portable controller including a housing, a power source mounted in said housing and generating direct current power, a microprocessor mounted in said housing and connected to said power source, said controller generating a direct current power signal and an oscillating input signal;

a portable fuel cell separate from said portable controller, said portable fuel cell including a container for receiving a sample of fuel to be tested, at least two generally parallel plates mounted in said container, a phase locking oscillator circuit connected to said plates, a direct current conductivity plate mounted in said container, a conductivity converter circuit connected to said conductivity plate, a thermocouple terminal probe mounted in said container, and a temperature converter circuit connected to said probe;

a cable connected between said portable controller and said portable fuel cell for applying said oscillating output signal to said phase locking oscillator circuit and for applying said direct current power signal to said conductivity converter circuit and to said temperature converter circuit;

whereby when a sample of fuel is placed in said container in contact with said plates and said probe, said temperature converter circuit generates through said cable a temperature control signal representing a temperature of the fuel sample, said conductivity converter circuit gets through said cable a conductivity control signal representing a conductivity of the fuel sample, and said phase locking oscillator circuit generates through said cable a resonant frequency control signal representing a resonant frequency of the fuel sample;

wherein said microprocessor is responsive to said temperature control signal for generating a temperature output signal representing the temperature of the fuel sample;

wherein said microprocessor is responsive to said resonant frequency control signal, said temperature control signal and said conductivity control signal for generating an oxygen output signal representing an oxygen mass weight percentage of the fuel sample; and wherein said microprocessor is responsive to said resonant frequency control signal, said temperature control signal and said conductivity control signal for generating a type output signal representing a probable additive type of the fuel sample and for generating a volume output signal representing an additive volume percentage of the fuel sample.

2. The system according to claim 1 including a display mounted in said housing and being connected to said microprocessor, said display being responsive to said temperature output signal for displaying information representing the temperature of the fuel sample, being responsive to said oxygen output signal for displaying information representing the oxygen mass weight percentage of the fuel sample, being responsive to said type output signal for displaying information representing the probable additive type of the fuel sample and being responsive to said volume output signal for displaying information representing the additive volume percentage of the fuel sample.

3. The system according to claim 1 including a keyboard mounted on said housing and being connected to said microprocessor for generating input signals to control said microprocessor.

4. The system according to claim 1 including a printer port connected to said microprocessor for connection to a printer being responsive to said temperature output signal for printing information representing the temperature of the fuel sample, being responsive to said oxygen output signal for printing information representing the oxygen mass weight percentage of the fuel sample, being responsive to said type output signal for printing information representing the probable additive type of the fuel sample and being responsive to said volume output signal for printing information representing the additive volume percentage of the fuel sample.

5. The system according to claim 1 including a computer connected to said microprocessor for receiving and processing said temperature output signal, said oxygen output signal, said type output signal and said volume output signal.

6. A portable fuel oxygenate additive analyzer system for field testing and analyzing oxygen and additive content in samples of fuels comprising:

a portable controller including a housing, a power source mounted in said housing and generating direct current power, a microprocessor mounted in said housing and connected to said power source, a phase lock loop circuit mounted in said housing and connected to said power source and to said microprocessor, said phase lock loop circuit generating a direct current power signal and an oscillating input signal;

a portable fuel cell separate from said portable controller, said portable fuel cell including a container for receiving a sample of fuel to be tested, a plurality of generally parallel plates mounted in said container and being electrically connected together in a first set of said plates and a second set of said plates in an alternating relationship, a phase locking oscillator circuit connected to said plates, a direct current conductivity plate mounted in said container, a conductivity converter circuit connected to said conductivity plate, a thermocouple terminal probe mounted in said container, and a temperature converter circuit connected to said probe;

a cable connected between said portable controller and said portable fuel cell for applying said oscillating output signal to said phase locking oscillator circuit and for applying said direct current power signal to said conductivity converter circuit and to said temperature converter circuit;

whereby when a sample of fuel is placed in said container in contact with said plates and said probe, said temperature converter circuit generates through said cable a temperature control signal representing a temperature of the fuel sample, said conductivity converter circuit generates through said cable a conductivity control signal representing a conductivity of the fuel sample, and said phase locking oscillator circuit generates through said cable a resonant frequency control signal representing a resonant frequency of the fuel sample;

wherein said microprocessor is responsive to said temperature control signal for generating a temperature output signal representing the temperature of the fuel sample;

wherein said microprocessor is responsive to said resonant frequency control signal, said temperature control signal and said conductivity control signal for generating an oxygen output signal representing an oxygen mass weight percentage of the fuel sample; and wherein said microprocessor is responsive to said resonant frequency control signal, said temperature control signal and said conductivity control signal for generating a type output signal representing a probable additive type of the fuel sample and for generating a volume output signal representing an additive volume percentage of the fuel sample.

7. The system according to claim 6 including at least one port connected to said microprocessor for generating signals to one of a printer and a personal computer.

* * * * *